United States Patent [19]

Gillard

[11] 4,329,585

[45] May 11, 1982

[54] X-RAY TUBE ARRANGEMENTS

[75] Inventor: Richard G. Gillard, Uxbridge, England

[73] Assignee: EMI Limited, Hayes, England

[21] Appl. No.: 123,755

[22] Filed: Feb. 22, 1980

[30] Foreign Application Priority Data

Mar. 21, 1979 [GB] United Kingdom ................. 7909847

[51] Int. Cl.[3] .......................... H05C 1/30; A61B 6/00

[52] U.S. Cl. ................................ 250/403; 250/445 T

[58] Field of Search .................. 250/402, 401, 445 T, 250/403

[56] References Cited

U.S. PATENT DOCUMENTS 4,112,397 9/1978 Randall .......................... 250/445 T 4,123,659 10/1978 Oliver ............................ 250/445 T 4,160,909 7/1979 Froggatt ......................... 250/445 T 4,211,925 7/1980 Fairbairn ........................ 250/445 T

*Primary Examiner*—Alfred E. Smith

*Assistant Examiner*—T. N. Grigsby

*Attorney, Agent, or Firm*—Cooper, Dunham, Clark, Griffin & Moran

[57] ABSTRACT

A technique for ensuring the rapid correction of both amplitude and offset errors in the deflectional movement of an electron beam along an X-ray emissive target is disclosed. The movement is monitored at at least two positions during a sweep and differences, between the two movements and a desired movement, at these positions are combined in unequal proportions to produce a corrective servo signal.

3 Claims, 7 Drawing Figures

X-RAY TUBE ARRANGEMENTS

The present invention relates to X-ray tube arrangements, and it relates more especially to such arrangements including an X-ray tube with an extended anode/target member and deflection means for repetitively deflecting the electron beam of the tube over the anode/target member with the object of repetitively and rapidly shifting the origin from which X-rays are emitted.

Such arrangements find application, for example, in medical diagnostic instruments known as computerised tomographic (CT) scanners. In such an application, the tube is bodily scanned around a cross-sectional slide of a patient's body and the deflection is effected at a relatively high rate compared with the bodily scanning. The two movements, i.e. the deflection and the scanning, are correlated so that their combined effect achieves a desired irradiation programme in relation to the body slice.

In order that the two movements may be accurately correlated, it will be appreciated that the progress of the deflection should be accurately monitored and that any departure from the desired progress should be corrected as rapidly as possible.

It is an object of this invention to provide an X-ray tube arrangement which permits such accurate monitoring and rapid correction to be achieved.

According to the invention there is provided an X-ray tube arrangement including an X-ray tube having an extended X-ray emissive target member, means for deflecting the electron beam of the tube to and fro across the target member, to cause the effective origin of the X-rays to perform a reciprocating movement over said member, monitoring means for monitoring said movement and for generating electrical signals indicative of the relationship between the monitored movement and a desired movement at a first position and at least one further position during a sweep, means for combining said electrical signals in different proportions, and means for utilising the combined signal to control the deflection of said beam so that the flyback tends to position the electron beam correctly for the start of the next sweep, and the next sweep is of the required amplitude.

Techniques for monitoring the progress of a deflectional movement and correcting for departures from a desired progress in the foregoing context are known. One such technique is disclosed in U.S. Pat. No. 4,123,659. Other techniques are described in U.S. Pat. Nos. 4,160,909 and 4,112,397 and in U.S. patent application Ser. No. 897,787 filed Apr. 19, 1978 and now U.S. Pat. No. 4,211,925.

The present invention represents an alternative to the techniques disclosed in the aforementioned patents and patent application and exhibits improved performance at least in respect of the rapidity of its corrective action.

In order that the invention may be clearly understood and readily carried into effect, one embodiment thereof will now be described by way of example only. In describing the invention and the background thereto reference will be made to the accompanying drawings, of which:

A basic requirement of the arrangement is the generation of a sawtooth waveform which, after amplification, is fed to deflection coils, causing the electron beam to repetitively sweep across the target of the tube. As the deflection waveform is essentially linear, two positional references are adequate to define the position of the electron beam at any time during a sweep and to that end, in a known arrangement, the outputs of two positional reference detectors, viewing the X-ray emissive target through respective slots, are compared with reference timing pulses in such a way that the resulting error signals are used to adjust the deflection waveform to the correct amplitude and offset. This arrangement is satisfactory provided that the sweep period does not alter quickly. If large variations in sweep periods are expected, the gain of the error adjustment must be increased. With high gain it is possible for the known arrangement to correct an amplitude error immediately, so that the amplitude is correct for the following sweep, but any offset error cannot be removed successfully until the amplitude is first corrected.

Figure 1:
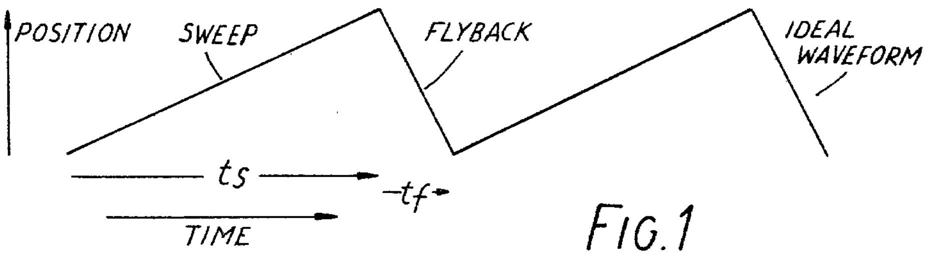
FIG. 1 shows an ideal sawtooth waveform.
Figure 2:
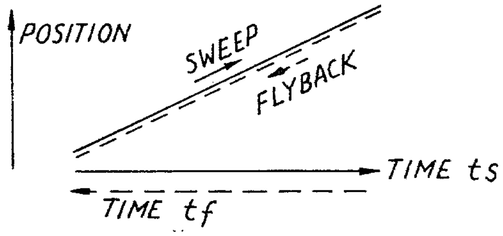
FIG. 2 shows a different representation of such a waveform.

FIG. 1 shows the ideal deflection waveform, and FIG. 2 represents the same waveform with the flyback shown on a reversed, expanded time scale in such a way that, for the ideal waveform, the flyback lies exactly on the sweep line. This representation enables the relative amplitudes and offsets of adjacent sweeps to be seen more easily.

Figure 3:
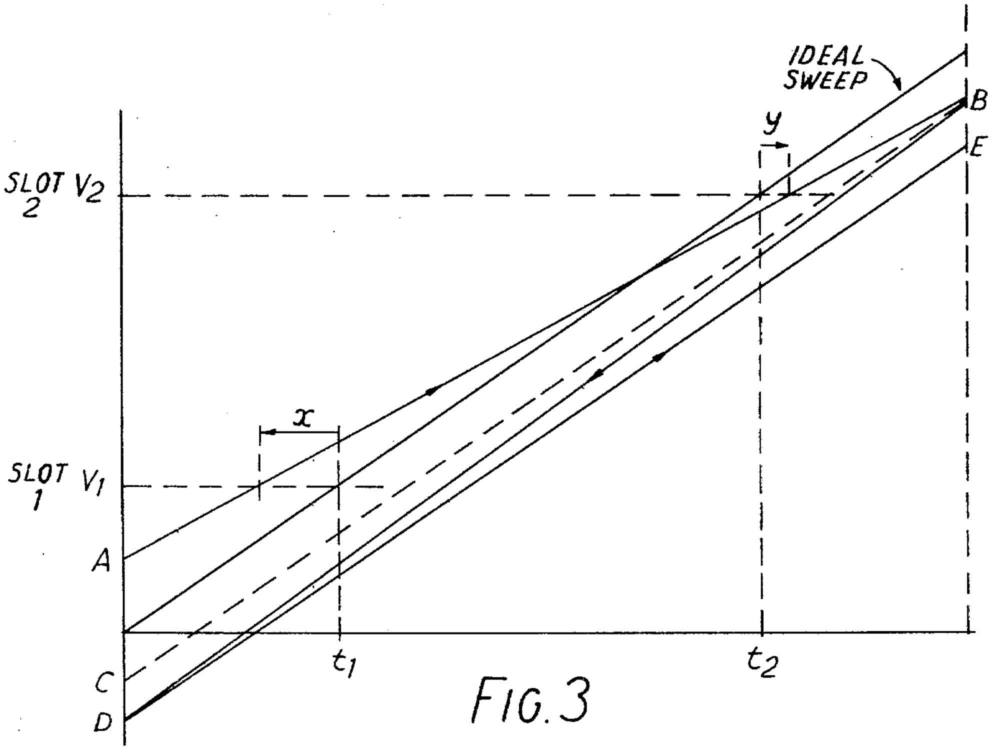
FIG. 3 shows waveform errors and illustrates how a known technique of error reduction can be slow in response.

FIG. 3 shows an example of sweep AB with amplitude and offset errors. Suppose the ideal sweep is such that the source is in line with the positional reference slots at time $t_1$ and $t_2$, requiring a voltage of $V_1$ and $V_2$ respectively on the input of the sawtooth amplifier. The amplitude correction is an accumulative correction, brought into effect at the beginning of flyback, whereas the offset correction, acting only during the flyback, is reset to zero at the beginning of the sweep. With the known arrangement the amplitude correction, proportional to $(x+y)$, would produce a flyback BC and a new sweep CB, parallel to the ideal line i.e. of the correct amplitude but with an offset error. In addition, the offset correction, proportional to $(x-y)$, would further adjust the flyback to follow line BD, so that the new sweep would be line DE, again of the correct amplitude. At least another sweep is required to remove the offset error. Often, as in this case, the offset correction after the first sweep alters the position of the next sweep in the wrong direction, since although the net offset of the first sweep $(x-y)$ is in one direction, the sweep finishes with an offset in the other direction which is not taken into account. As indicated earlier, difficulties of rapidly correcting both amplitude and offset are exacerbated in circumstances where the sweep period exhibits large variations.

In accordance with an example of the invention, the error signals x and y are utilised such that sweep errors can be corrected almost immediately.

Figure 4:
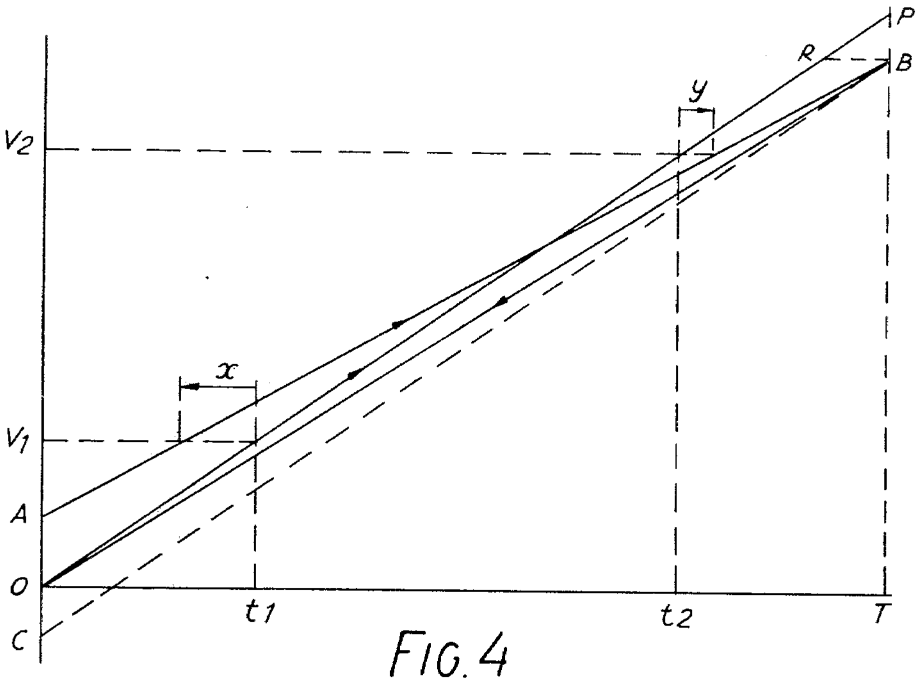
FIGS. 4 and 5 are similar to FIG. 3, but show how the invention can be used to speed up error correction.
Figure 5:
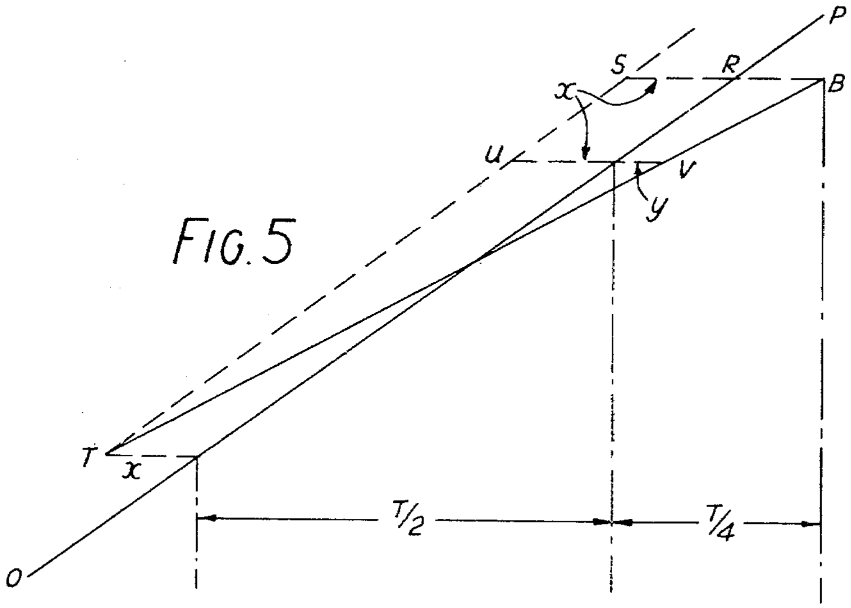

Referring now to FIG. 4, there is shown again the sweep AB with errors x and y. Once again, with amplitude correction only, the flyback would take path BC. However, if the flyback path could be made to conform to BO, then on the next sweep OP the amplitude would be correct and the offset would be zero. In order to cause the flyback path to follow BO, an offset correction proportional to CO is required. CO equals BP which in turn is roughly proportional to RB. RB is related to errors x, y and $t_1$, $t_2$ as shown below, and explained with reference to FIG. 5.

Suppose $t_1$ equals T/4 and $t_2=3T/4$, where T is the sweep duration. Construct a line TS parallel to OP. From similar triangles TUV and TSB it can be seen that $$\frac{3}{2}(x+y) \approx x + RB$$

(remembering x and y are small) so $$RB \approx \frac{(x+3y)}{2}$$

where $\approx$ indicates approximate equality

Thus if the offset correction is made proportional to (x+3y) the shift error can be removed immediately, together with any amplitude error. Similarly, whatever the relationship between $t_1$ and $t_2$ and the sweep duration T, the contribution of x and y to the offset correction can be adjusted accordingly. In general therefore, this principle enables rapid control of a continuous sawtooth waveform using two error signals.

In practice the control circuits utilising these error signals could be digital or analogue.

In a digital system, the timing errors could be converted into counts and fed to a microprocessor, the output of the latter driving a digital to analogue converter to produce the required sawtooth.

Figure 6:
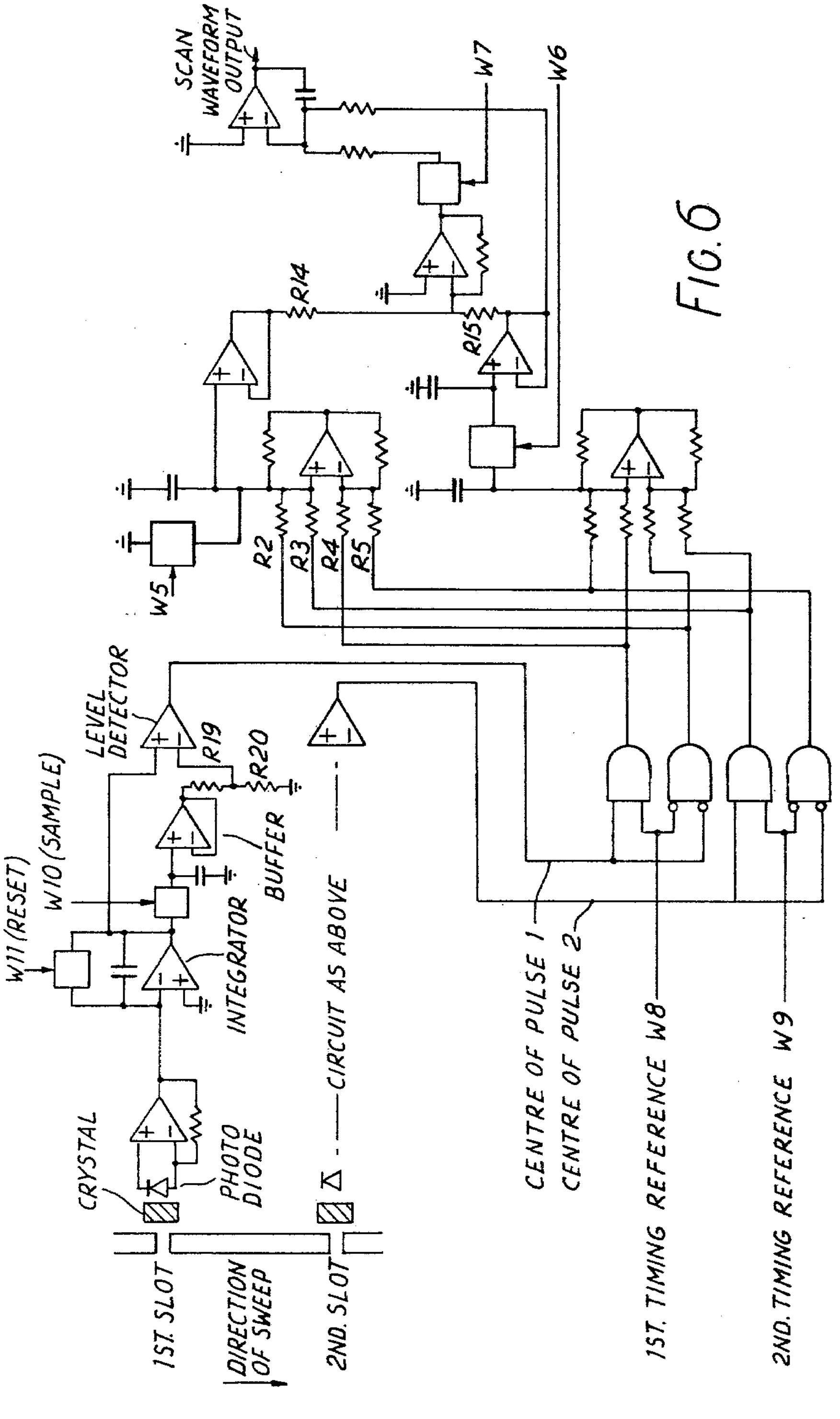
FIG. 6 shows a circuit arrangement for achieving the invention.

Details of an analogue system are shown in FIG. 6. The circuit is similar to that shown in FIG. 8 of U.S. Pat. No. 4,123,659 (which explains in detail the operation of the circuit). Components of FIG. 6 to which no specific reference is made herein are the same as the corresponding components in the aforementioned FIG. 8 and operate as described in U.S. Pat. No. 4,123,659. The circuit of FIG. 6 is modified, compared with said FIG. 8, in that some of the timing pulses and waveforms to which it responds differ from those described in the aforementioned U.S Pat. No. 4,123,659, and also that the resistances of resistors R2, R3, R4, R5 in the offset or "shift" current generator circuit are selected to take account of the unequal contributions required from the x and y errors. Also, in the circuit shown in said FIG. 8, unless the positional reference pulses straddled the reference timing edges, the true magnitude of the errors could not be taken into account. For example, it would be known that a pulse occurred before a timing edge, but there would be no indication of the actual time between the pulse and the timing edge. If edges are generated representing the centres of the positional reference pulses then the time between these edges and the timing reference points represent exactly the errors x and y. This enables the new principle to be put to effective use since reasonably large errors can be quickly removed.

One convenient technique for permitting the times to be accurately monitored involves the production of square wave signals commencing at the centres of the pulses produced by the first and second positional reference detectors. These square wave signals are referred to as "centre of pulse" signals. A reference detector pulse signal generated during one sweep is integrated and the level stored. During the next sweep, a level detector produces an edge when the new integration reaches half the stored level, i.e. the centre of the pulse (provided the pulse retains a reasonably constant size between adjacent sweeps). In FIG. 6 R19 and R20 define half the stored level, so these resistors must be equal in value. If the offset correction is proportional to (x+3y), then R2=R4=3R3=R5. The details of the remaining circuit components are described in the previously mentioned Patent, thought it will be appreciated that, in the present example, two detectors with respective slots are used instead of one large detector which views both slots. Clearly either construction could be used as convenient.

Figure 7:
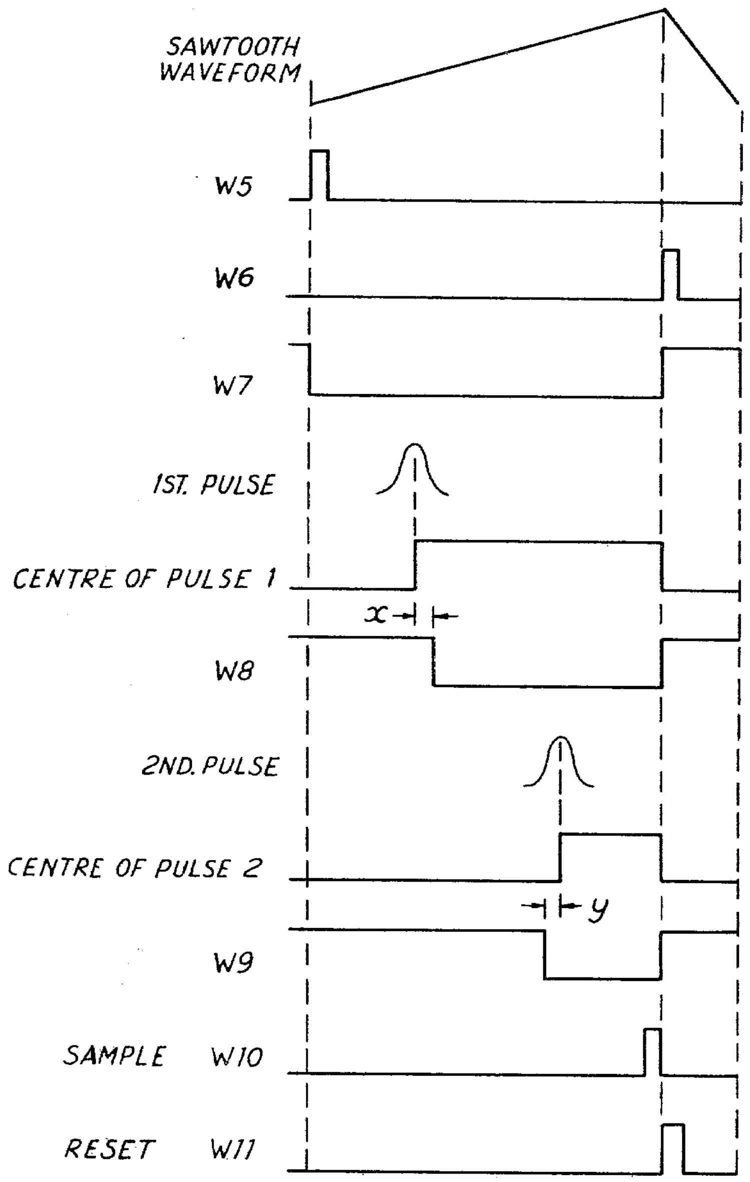
FIG. 7 shows waveforms applied to various points in the circuit of FIG. 6.

Appropriate waveforms are shown in FIG. 7 which is, it is believed, self explanatory when considered in conjunction with FIG. 6. The waveforms marked Wn, where n represents a number, are applied to the correspondingly designated points in the circuit of FIG. 6.

In an embodiment of the invention which has been used in practice, it has been found desirable to incorporate a linearity correction which pre-distorts the sawtooth to remove some of the non-linearity effects in the x-ray tube. Also, with faster scan speeds, appropriate adjustments must be made to the circuit to retain the required loop gain. In addition, a low gain signal can be used to cause the servo action of the circuit to operate in a low gain state so that it is less sensitive to noise. This low gain state can, of course, only be used with a reasonably stable sweep period and when a good 'lock' has already been achieved.

If the ratio of the charging and discharging currents into the sawtooth generating integrator does not exactly match the ratio of sweep to flyback times, a small offset will occur in the sawtooth, which in turn will provide the slight adjustment required in the discharging current. However when switched to low gain, a much larger offset would be required to produce this compensation. To prevent this a circuit can be incorporated which monitors the average offset error when working at high gain, and feeds this through a separate current path when switched to low gain. In this way, the average offset can be caused to remain constant.

What we claim is:

1. Monitoring means for monitoring repeated deflectional movements, consisting of alternate forward sweeps and flyback movements, executed by the electron beam of an X-ray tube relative to an extended x-ray emissive target member of the tube, the monitoring means including first and second X-ray detector means arranged to receive radiation respectively from first and second locations spaced apart along the path followed by said beam across said target member in performing said deflectional movements, and to generate respective electrical signals when the electron beam occupies said locations, means for utilising said electrical signals to generate respective error signals indicative of departure of the actual deflectional movement of said electron beam from its desired forward sweep movement, means for generating a combined signal consisting of unequal proportions of said respective error signals and means for utilising said combined signal to control the deflection of said beam so that the next flyback movement positions the electron beam correctly for the start of the next forward sweep, and the next forward sweep is of the desired amplitude.

2. Monitoring means as claimed in claim 1 wherein said first and second locations are located approximately one quarter and approximately three quarters respectively of the distance along the ideal forward sweep path followed by said electron beam across said target member.

3. Monitoring means as claimed in claim 2 wherein said different proportions in which said electrical signals are combined are in the ratio of approximately 3:1.

* * * * *